(12) United States Patent
Sarstedt

(10) Patent No.: US 8,096,958 B2
(45) Date of Patent: Jan. 17, 2012

(54) BLOOD-COLLECTION DEVICE FOR NEWBORN BABIES AND INFANTS

(75) Inventor: Walter Sarstedt, Nümbrecht (DE)

(73) Assignee: Sarstedt AG & Co, Numbrecht (DE)

( * ) Notice: Subject to any disclaimer, the term of this patent is extended or adjusted under 35 U.S.C. 154(b) by 106 days.

(21) Appl. No.: 10/593,171

(22) PCT Filed: Feb. 4, 2005

(86) PCT No.: PCT/DE2005/000180
§ 371 (c)(1),
(2), (4) Date: Jul. 21, 2008

(87) PCT Pub. No.: WO2005/089650
PCT Pub. Date: Sep. 29, 2005

(65) Prior Publication Data
US 2008/0281227 A1    Nov. 13, 2008

(51) Int. Cl.
*A61B 5/00* (2006.01)
*B65D 81/00* (2006.01)
*A61M 5/32* (2006.01)

(52) U.S. Cl. .................. 600/576; 600/573; 604/272

(58) Field of Classification Search .......... 600/576–579, 600/573, 575, 581, 583; 604/6.16, 507, 8.01, 604/187, 177–179, 263, 105, 188, 272–274, 93.01; 33/813–831
See application file for complete search history.

(56) References Cited

U.S. PATENT DOCUMENTS

| | | | | |
|---|---|---|---|---|
| 2,437,408 A * | 3/1948 | Soet | .............................. | 600/577 |
| 4,844,089 A | 7/1989 | Roberti | ......................... | 600/577 |
| 4,976,271 A * | 12/1990 | Blair | .............................. | 600/577 |
| 5,086,782 A | 2/1992 | Zucker | ......................... | 600/578 |
| 5,092,461 A * | 3/1992 | Adam | ........................... | 206/365 |

FOREIGN PATENT DOCUMENTS

| | | |
|---|---|---|
| DE | 3802353 | 8/1989 |
| DE | 10060302 | 6/2002 |
| EP | 0732077 | 9/1996 |
| WO | WO 9220281 A1 * | 11/1992 |

* cited by examiner

Primary Examiner — Max HIndenburg
Assistant Examiner — John Pani
(74) Attorney, Agent, or Firm — Andrew Wilford

(57) ABSTRACT

The invention relates to a blood-collection device for newborn babies and infants, comprising a cannula, which is provided with a blood inlet and outlet and is located in a holder (2) that has a grip region (7). Said collection device is equipped with a bow-shaped bridging element (6) that connects the grip region to the holder.

2 Claims, 1 Drawing Sheet

BLOOD-COLLECTION DEVICE FOR NEWBORN BABIES AND INFANTS

CROSS REFERENCE TO RELATED APPLICATIONS

This application is the U.S. national phase of PCT application PCT/DE2005/000180, filed 4 Feb. 2005, published 29 Sep. 2005 as WO2005/089650, and claiming the priority of German patent application 102004013379.4 itself filed 17 Mar. 2004, whose entire disclosures are herewith incorporated by reference.

FIELD OF THE INVENTION

A blood-collection device for newborn babies and infants, comprising a cannula provided with a blood inlet and outlet and mounted in a holder that has a grip part.

BACKGROUND OF THE INVENTION is Such a device for collecting venous blood from newborn babies and/or premature babies and infants is known from DE 100 60 302 A1. The hollow needle or cannula, which at its distal end is provided with a sharpened tip, at the rear, proximal end has a transversely open blood outlet, and is provided in a holder, whose grip part is oriented behind the blood outlet and offers the option of touching and/or guiding the holder. When collecting blood, a vessel is held below the outlet opening of the cannula, in order to collect the out-flowing blood.

Unlike with conventional injection needles, the cannula of this blood-collecting device does not require special preparation, e.g. it no longer is necessary to break off the Luer cone, as is normally necessary, thus reducing the risk of infection for patients and reducing the risk of injury and infection for the person collecting blood. However, visual monitoring of the quantity of blood to be collected is very inadequate, because with these small blood-collection devices, the grip and/or the finger of a person collecting blood considerably limits the view of the outlet opening and may even cover it. The transversely open outlet opening also results in the cannula only being able to ensure an optimal blood outlet in only one position of application. Apart from the fact that the production of an arcuate laterally angled cannula is costly, it also has the disadvantage that the higher flow resistance of the cannula impedes the flow of blood taken in a small quantity in any case, due to the bend in the cannula.

OBJECT OF THE INVENTION

In view of the foregoing, it is the object of the present invention to create a blood-collecting device of this type with which the above-described disadvantages can be avoided and which improves the user-friendliness.

SUMMARY OF THE INVENTION

This object is achieved according to the invention by means of a bow-shaped bridging element connecting the grip part with the cannula holder. Consequently, several advantages can be achieved simultaneously. The outlet end of the cannula is easy to see in the open space of the bridging element. Losing part of the small quantity of blood collected due to impaired view will not happen. Since the inlet and outlet openings of the cannula are positioned on the same axis, there are no bends and branches and there will be no loss due to friction, which could make the taking of blood from premature or newly born babies, infants or toddlers more difficult due to low blood pressure and low blood volume.

The bridging element also creates a free space that enables a relatively large collecting vessel to be placed underneath the outlet opening. The vessel ensures that even the smallest quantity of blood can be collected without loss. The free view of the outlet opening makes it possible to realize immediately when the first drop of blood flows. The handling of the inventive blood-collecting device is considerably simplified and safer, because the clear view of the cannula ensures its targeted insertion into the vein. Furthermore, especially when the blood- collecting device can be turned easily in the vein, in order to achieve an optimal blood inlet, and to prevent the ventricular wall from coming to rest on the angled opening and/or pointed section of the cannula, by which the opening is closed. In spite of the thus created option of rotation, the position of the outlet opening does not change, so that an optimal outflow of blood is guaranteed with any angular position. By contrast, a cannula with a bend and/or a branch only opens in one optimal position of use, in which the blood can flow out.

All other positions make the outflow of blood more difficult, and under certain circumstances, even impossible, for instance, if the outlet opening points upward.

BRIEF DESCRIPTION OF THE DRAWING

Additional features and details of the invention are described in the claim and the following description of an embodiment of the invention as shown in the drawings. Therein:

SPECIFIC DESCRIPTION

Figure 1:
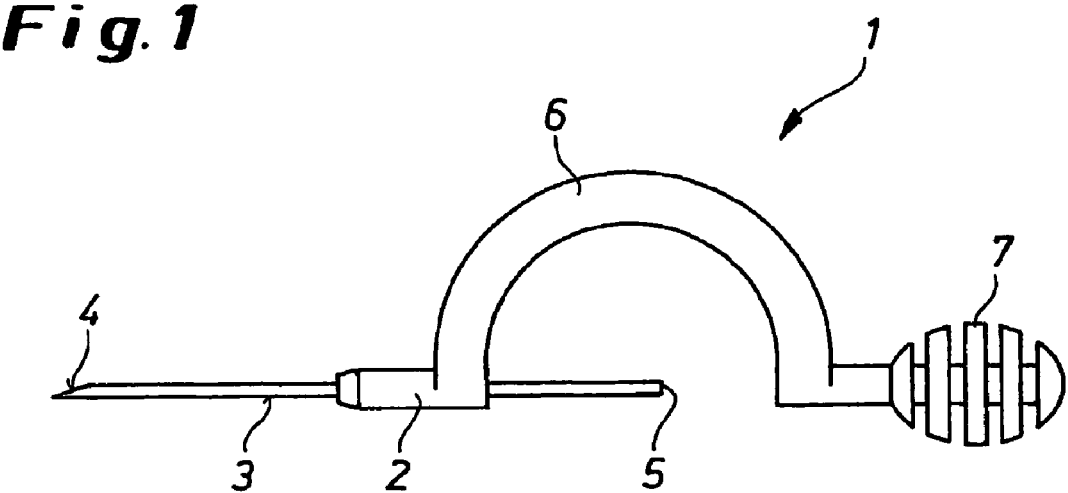
FIG. 1 is a side view of a blood-collecting device.
Figure 2:
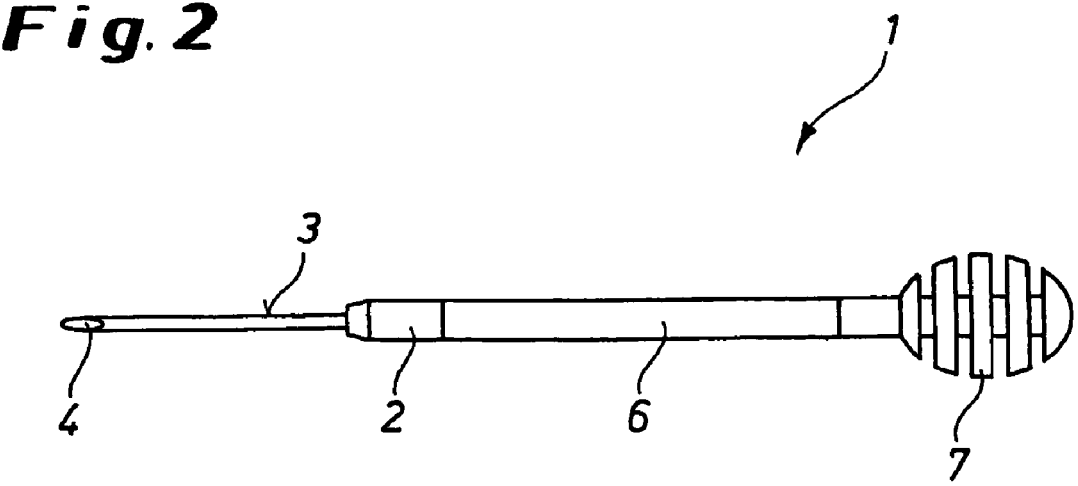
FIG. 2 is a top view of the blood-collecting device according to FIG. 1.

As shown in the figures, a blood-collecting device 1 comprises a hollow needle or cannula 3 provided in a holder 2 that has a front end provided with a sharpened tip 4 serving as a blood inlet for insertion into a vein, and at the opposite, proximal end a blood outlet 5. The blood outlet 5 is positioned in a large free space formed by a bow-shaped bridging element 6 that connects the cannula holder 2 with the grip part 7 of the blood-collecting device 1.

The connecting bridging element 6 enables a smooth rotation of the blood-collecting device with a cannula 3 inserted with its tip 4 into a vein, and offers to the operator a large clearly visible area with the option of using a large collecting vessel, and being able to recognize immediately the first drop of flowing blood, so that the smallest quantity of blood can be collected without loss.

As shown in FIG. 1, the grip part 7 has an outer surface that is centered on the axis of the cannula 3.

The invention claimed is:

1. A blood-collecting device for newborn babies and infants, the device comprising:
   a cannula extending along an axis and having at one axial end a blood inlet and at an opposite axial end a blood outlet;
   a bow-shaped bridge element having a front end in which the cannula is fixed and a rear end through which the axis passes and defining with the front end a free space, the cannula outlet being exposed between the front and rear ends in the free space and the inlet being outside the free space; and a grip part centered on and substantially rotationally symmetrical about the axis and fixed on the rear end of the bridge element rearward of the rear end and outside the free space.

2. The device defined in claim 1 wherein the bridge element is C-shaped.

* * * * *